US007368611B2

(12) United States Patent
Barth et al.

(10) Patent No.: US 7,368,611 B2
(45) Date of Patent: May 6, 2008

(54) PROCESS FOR THE CONTINUOUS PRODUCTION OF METHYLMERCAPTAN

(75) Inventors: Jan-Olaf Barth, Frankfurt am Main (DE); Hubert Redlingshöfer, Münchsteinach (DE); Christoph Weckbecker, Gründau-Lieblos (DE); Klaus Huthmacher, Geinhausen (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/278,894

(22) Filed: Apr. 6, 2006

(65) Prior Publication Data

US 2006/0229474 A1    Oct. 12, 2006

(30) Foreign Application Priority Data

Apr. 9, 2005    (DE) .................. 10 2005 016 369

(51) Int. Cl.
*C07C 381/00*    (2006.01)

(52) U.S. Cl. ....................................... 568/71
(58) Field of Classification Search ................. 568/71
See application file for complete search history.

(56) References Cited

U.S. PATENT DOCUMENTS 3,053,902 A  *   9/1962   Doumani .................... 568/71
5,886,230 A  *   3/1999   Hofen et al. ............... 568/71

FOREIGN PATENT DOCUMENTS

| DE | 1 134 368 | | 8/1962 |
| DE | 1 768 826 | | 8/1971 |
| DE | 196 54 515 C1 | | 10/1998 |
| DE | 196 54 516 C1 | | 10/1998 |
| EP | 0 832 687 A2 | | 4/1998 |
| EP | 0 850 922 A1 | | 7/1998 |
| FR | 2 477 538 | | 9/1981 |
| GB | 1 417 532 | | 12/1975 |
| GB | 1417532 | * | 12/1975 |
| WO | WO 2005/021491 A1 | * | 3/2005 |

* cited by examiner

*Primary Examiner*—Yvonne Eyler
*Assistant Examiner*—Sudhakar Katakam
(74) *Attorney, Agent, or Firm*—Robert G. Weilacher; Smith, Gambrell & Russell

(57) ABSTRACT

The invention relates to a process for the continuous production of methylmercaptan by reacting a starting gas mixture of methanol and hydrogen sulphide in the gas phase at a reaction temperature between 200 and 600° C. and an operating pressure of 1.5 to 40 bar on a catalyst in a multi-bed reactor.

22 Claims, 2 Drawing Sheets ature of 200 to 600° C. and an operating pressure of 1.5 to 40 bar on a catalyst in a multi-bed reactor.

PROCESS FOR THE CONTINUOUS PRODUCTION OF METHYLMERCAPTAN

INTRODUCTION AND BACKGROUND

The invention relates to a process for the continuous production of methylmercaptan by reacting a starting gas mixture of methanol and hydrogen sulphide in the gas phase at a reaction temperature of between 200 and 600° C. and an operating pressure of 1.5 to 40 bar on a catalyst in a multi-bed reactor.

Methylmercaptan is an industrially important intermediate for the synthesis of methionine and for the production of dimethyl sulphoxide and dimethyl sulphone. Methylmercaptan is mainly produced from methanol and hydrogen sulphide by reaction on a catalyst consisting of an alumina support and transition metal oxides and basic promoters. The synthesis of the mercaptan is usually carried out in the gas phase at temperatures between 300 and 500° C. and at pressures between 1 and 25 bar. The reaction of hydrogen sulphide and methanol to give methylmercaptan is an exothermic process. DE-C 196 54 515 describes, for example, a process for the production of methylmercaptan in a tube bundle reactor, in which the liberated heat of reaction is dissipated by means of a salt melt and is then utilized indirectly by means of heat exchangers for the evaporation of methanol.

In addition to the methylmercaptan formed and water, the product gas mixture contains the unreacted starting substances methanol and hydrogen sulphide and, as by-products, dimethyl sulphide and dimethyl ether, and in small amounts also polysulphides (dimethyl disulphide). In accordance with the reaction, inert gases such as, for example, carbon monoxide, carbon dioxide, nitrogen and hydrogen are also present in the product gas.

The methylmercaptan formed, as explained in DE 17 68 826, is separated off from the product gas mixture in a number of distillation and scrubbing columns at temperatures between 10 and 140° C.

The reaction according to GB 14 17 532 can be carried out in a fixed bed reactor containing a number of catalyst beds or in a number of consecutive reactors. Methylmercaptan is prepared here by the reaction of a mixture of methanol with hydrogen sulphide in a molar ratio of 1.10:1 and 2.5:1, both reaction components being fed to the reactor separately. According to FR 24 77 538, for the production of methylmercaptan fresh hydrogen sulphide gas is compressed to 11 bar in a compressor. Afterwards, cycle gas led back from the process, which contains hydrogen sulphide, dimethyl sulphide, methanol and small amounts of methylmercaptan, is mixed with the compressed hydrogen sulphide for the formation of the starting gas mixture and this is heated to 510° C. Before entry into the first of up to 10 reactors connected in series, the washing agent cycle stream, which contains methanol and dimethyl sulphide, is admixed to the starting gas mixture, whereby the reaction entry temperature falls to 450° C. Before the second and the following reactors, further methanol, partly as a liquid and partly as a gas, is injected into the gas stream.

DE-C 11 34 368 relates to the use of a tube bundle reactor for the production of methylmercaptan. The reactor consists of a cylindrical container, in which the catalyst tubes are arranged parallel to one another. The catalyst tubes are welded below and above with tube cover plates, as in tube bundle heat exchangers, the intermediate spaces between the tubes being filled with heat-conducting fluid. Each catalyst tubes is provided at its lower end with a screen, which carries the particulate catalyst.

DE 196 54 515 relates to a process for the production of methylmercaptan, in which the energy needed for the evaporation of the methanol is partly introduced by utilization of the heat of compression of the hydrogen sulphide gas and by the heat content of the product gas leaving the reactor. The heat of reaction is utilized here in order to heat the starting gas mixture to the reaction temperature with the aid of an external gas heater.

The economy of the overall process depends crucially on the reaction of the starting gas mixture in a suitable pressure reactor and the preparation of this gas mixture. For example, large electrical powers are needed for the operation of the compressors and of the heating and cooling circuits. Further, expensive changes of catalyst in tube bundle reactors on account of long stoppage times represent a time and cost factor which is not to be neglected.

The object of the invention is the provision of an economic process for the production of methylmercaptan.

SUMMARY OF THE INVENTION

The invention relates to a process for the continuous catalysed production of methylmercaptan by reaction of methanol and hydrogen sulphide in the gas phase at a temperature of 200 to 600° C., in particular 250 to 500° C. and a pressure of 1.5 to 40 bar, where a) the total amount of catalyst is distributed equally or unequally to at least two, preferably at least three, zones which are separate from one another, b) the first of these zones is supplied with a gaseous mixture comprising methanol and hydrogen sulphide (starting gas), c) between the first, the second and optionally the further zones, methanol is fed in liquid and/or gaseous form, and d) the methylmercaptan formed is separated off, the overall molar ratio of the amounts of hydrogen sulphide and methanol employed amounting to 1:1 to 10:1, preferably 1:1 to 5:1, particularly preferably 1.1:1 to 3:1.

The gaseous mixture of hydrogen sulphide and methanol (starting gas) contains these two compounds in a molar ratio of 1.1:1 to 20:1, preferably 1.1:1 to 10:1, in particular 3:1 to 10:1 and optionally by-products from the reaction and inert gases, if, for example, unreacted components are separated off from the product gas stream together with these compounds and recycled.

The use of this starting gas guarantees even in the first catalyst bed thorough mixing of the reactants and a heat of reaction, generated by the high conversion, which is employed for the evaporation of the methanol fed in after the first zone. If, as customary according to the prior art (GB 14 17 532), methanol is fed in even before the first zone, evaporation energy must additionally be supplied.

Likewise, the methanol fed in between the zones containing the catalysts can contain sulfur-containing starting materials or products, but consists essentially (in general >90 mol %) of methanol.

Preferably, an operating pressure of 2.5 to 25 bar is set.

The compression of the starting gases to the operating pressure is carried out in one or more stages.

In the first catalyst-containing zone, the hydrogen sulphide is always present in an excess compared to methanol.

The total amounts of the methanol fed in the starting gas and between the zones are in the ratio from 1:1 to 1:10, preferably 1:2 to 1:7.

Preferably, grid reactors are employed which contain 2 to 25 catalyst beds (zones), in particular 3 to 10, preferably 3 to 8.

At the same time, also at least two of these reactors can be connected to one another.

Grid reactors allow the direct metering in of gaseous and liquid methanol, hydrogen sulphide or a starting gas mixture containing, inter alia, methanol and hydrogen sulphide between the catalyst beds (grids), where the heat of reaction liberated in the grids is utilized directly for the evaporation of the methanol, and the temperature of the gas mixture drops before entry into the next grid. As a result of this concept, powerful methanol evaporators can be dispensed with. The economy of the overall process is also made possible in comparison with tube bundle reactors (with thousands of individual tubes to be filled and emptied), by more rapid modular catalyst exchanges in the grids. Thus the catalyst of each grid can be exchanged separately. This is particularly advantageous if the deactivation of the catalyst, as in the synthesis of methylmercaptan, is dependent on the concentrations of the reactants and thus on the site or reaction progress. Furthermore, the use of various catalysts in a reactor is facilitated thereby.

As a result of the use of the grid reactor, especially in reactions with very strong evolution of heat, such as, for example, the synthesis of methylmercaptan from methanol and hydrogen sulphide by means of catalysts customary for the process, excellent temperature control is possible by choice of the grid size and the amount of injected liquid. By this means, in the synthesis of methylmercaptan, high excess temperatures, which lead to decreased yields and to an increased deactivation of the catalyst, can be avoided.

BRIEF DESCRIPTION OF DRAWINGS

FIG. 1 shows a process scheme of the first section of the production process of methylmercaptan.

FIG. 2 shows a detail representation of a grid reactor used in this process.

DETAILED DESCRIPTION OF INVENTION

Figure 1:
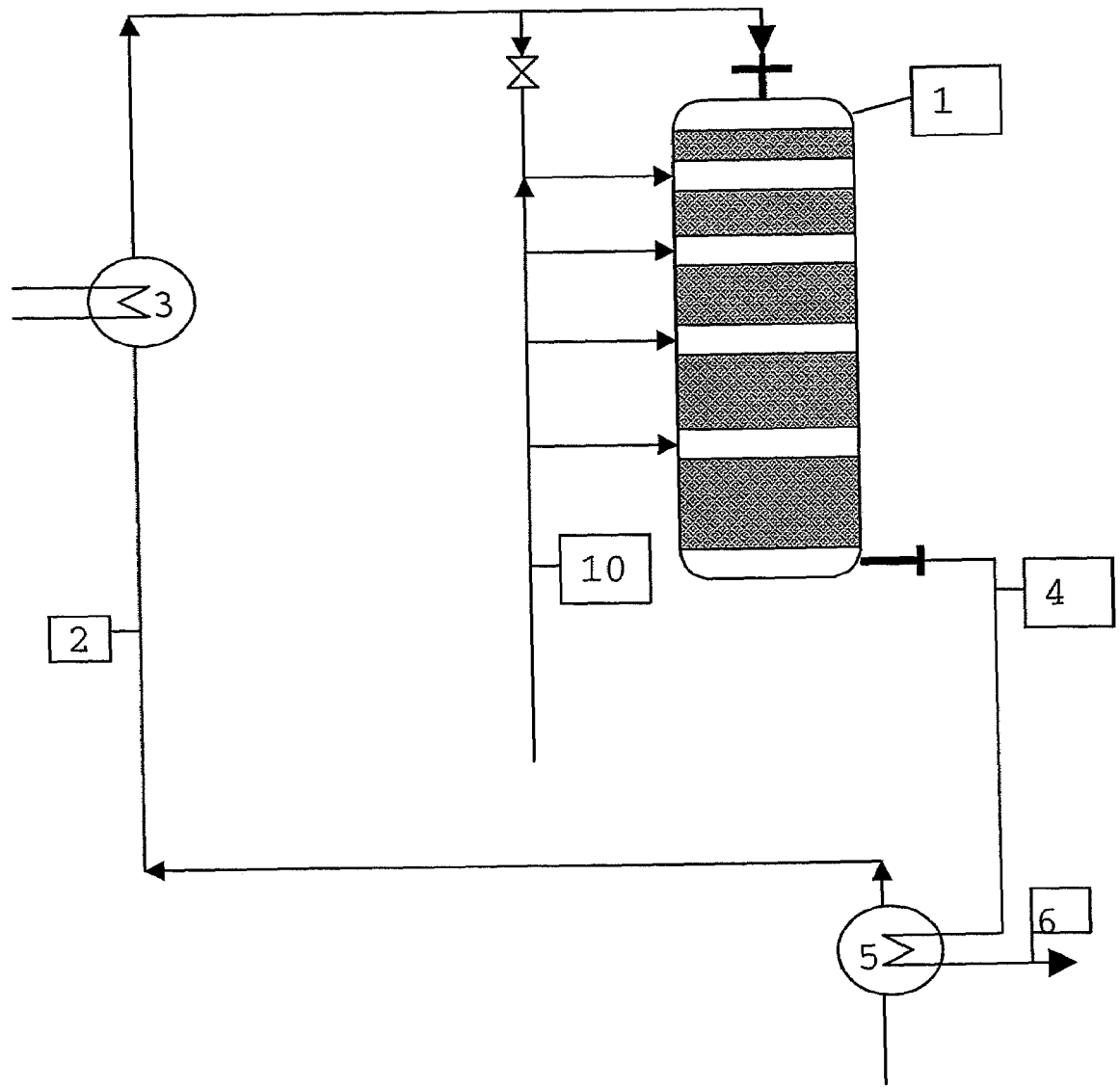
FIG. 1 and FIG. 2 serve for the further explanation of the process using the preferably employed grid reactor.

FIG. 1 shows a process scheme for the first section of the methylmercaptan production, which comprises the starting gas preparation, the reaction in the reactor and the cooling of the product gas mixture. The reaction in the grid reactor 1 is carried out on customary catalysts, preferably on alumina, as a carrier, which are preferably coated with alkali metal tungstate, in particular caesium tungstate. The catalysts are described in the applications WO 2005/021491, DE 10 2004 77 39 and DE 10 2004 061 016.

Catalysts of this type are able to react a starting gas mixture having a molar ratio of hydrogen sulphide to methanol of 1.5:1 to 10.0:1 at an operating pressure of 5-20 bar, a reaction temperature of 280-450° C. and at a loading with a space rate GHSV of 300-2000 h-1 with a methanol conversion and a selectivity of in each case more than 90% to give methylmercaptan. The process according to the invention also allows the preparation of methyl-mercaptan using otherwise customary catalysts.

On account of the very active catalysts for the synthesis of methylmercaptan, which especially contain halide-free alkali metal tungstates, halide-containing alkali metal tungstates or preferably halide-free or -containing caesium tungstates as promoters, an excellent temperature control for the operation of these catalysts at the yield optimum, without an increased deactivation of the catalyst having to be feared, is necessary. This is made possible when using these and other customary catalysts and carrying out according to the invention the synthesis in a grid reactor.

The starting gas mixture 2 consisting of methanol vapour, hydrogen sulphide and optionally further of the above-mentioned components is heated in the gas heater 3 to the reactor entry temperature (pre-temperature) of 100-350° C. The starting gas mixture reaches the grid reactor at this temperature.

On account of the quantitative proportion of methanol and hydrogen sulphide, the starting gas mixture cannot be confused with a hydrogen sulphide gas which contains small amounts of methanol as a result of recycling.

The gas mixture is dispersed uniformly over the catalyst bed of the first reactor grid by means of dispersing devices. For better heat transfer, the catalyst bed of the first reactor grid is optionally covered with a layer of inert, solid packing materials, at least in the area of the entry of the gas stream. Advantageously, for this, for example, packing material spheres of ceramic, silica or alumina are used. The grid reactor in general contains 2 to 25 catalyst beds, advantageously 2 to 10 catalyst beds, preferably 3-8, are accommodated in one apparatus. Between the grids, liquid or optionally gaseous methanol, optionally also hydrogen sulphide or the starting gas mixture 2 is metered into the process. Methanol is preferably fed to the process in liquid form between all grids or some of the grids. At the same time, the heat of reaction which is released in the grid situated before the injection site is utilized for the evaporation of the methanol and for the control of the temperature in the strongly exothermic reaction.

A lengthening of the bed length of the catalyst grids or an increase in the amount of catalyst from the first to the last grid (zone) in the flow direction has proved advantageous. Optionally, no methanol is fed in before the last grid.

Between the catalyst grids are optionally situated devices, such as, for example, static mixers, ordered or disordered packings, which make possible a turbulent flow course and a uniform dispersion and mixing of the reactants. Preferably, the starting gas mixture optionally metered in between the catalyst grids and/or the liquid methanol is dispersed radially, tangentially or zone-wise over the catalyst bed by means of a gas disperser, so that a uniform turbulent flow distribution and complete mixing of the reactants results. The mixing of the reactants can be improved by optional introduction of inert layers of packing materials.

The catalyst grids are advantageously designed as catalyst beds having radial, square or polygonal geometry, other geometries also being possible. The grids can individually be filled with catalyst or emptied. Preferably, they are designed such that they can be removed from the reactor in modular form. Alternatively, in each case a detachable or undetachable connection or opening in the reactor wall can be utilized for the simple exchange of the catalyst.

In a further embodiment of the invention, the grids are filled with at least two different catalysts. The dependence of the local yield and local selectivity, especially in the synthesis of methylmercaptan, is thus taken into account as a function of the concentrations of the reactants and thus the progress of the reaction. For example, it is advantageous in the synthesis of methylmercaptan to fill the last grid with a very active catalyst if a complete conversion of methanol is desired. If the reaction is to be operated with respect to maximum selectivity, a less active, but for this very selective catalyst can be employed in the last grid. The grid reactor thus makes possible, by means of simple, site-dependent filling, flexibility in the production of methylmercaptan.

The product gas mixture 4 leaves the reactor at the reaction temperature of the last grid. Its heat content can be utilized in the heat exchanger 5 for the evaporation of methanol or for the production of steam etc. In this process, the product gas mixture cools to approximately 150° C. and is fed to the second process section as a volume flow 6. The separation of the product gas mixture into its components is performed in the second process step of the methylmercaptan production. The separation can be carried out according to various, known processes. A particularly advantageous separation of the product gas mixture is described in German patent specification DE-C 196 54 516. The leading back of the hydrogen sulphide separated off in the second process step as a cycle gas stream is important for the economy of the process. The same applies for the methanol separated off from the product gas mixture and not completely consumed in the reaction in the reactor, and for the wash methanol optionally used in the second process step.

Figure 2:
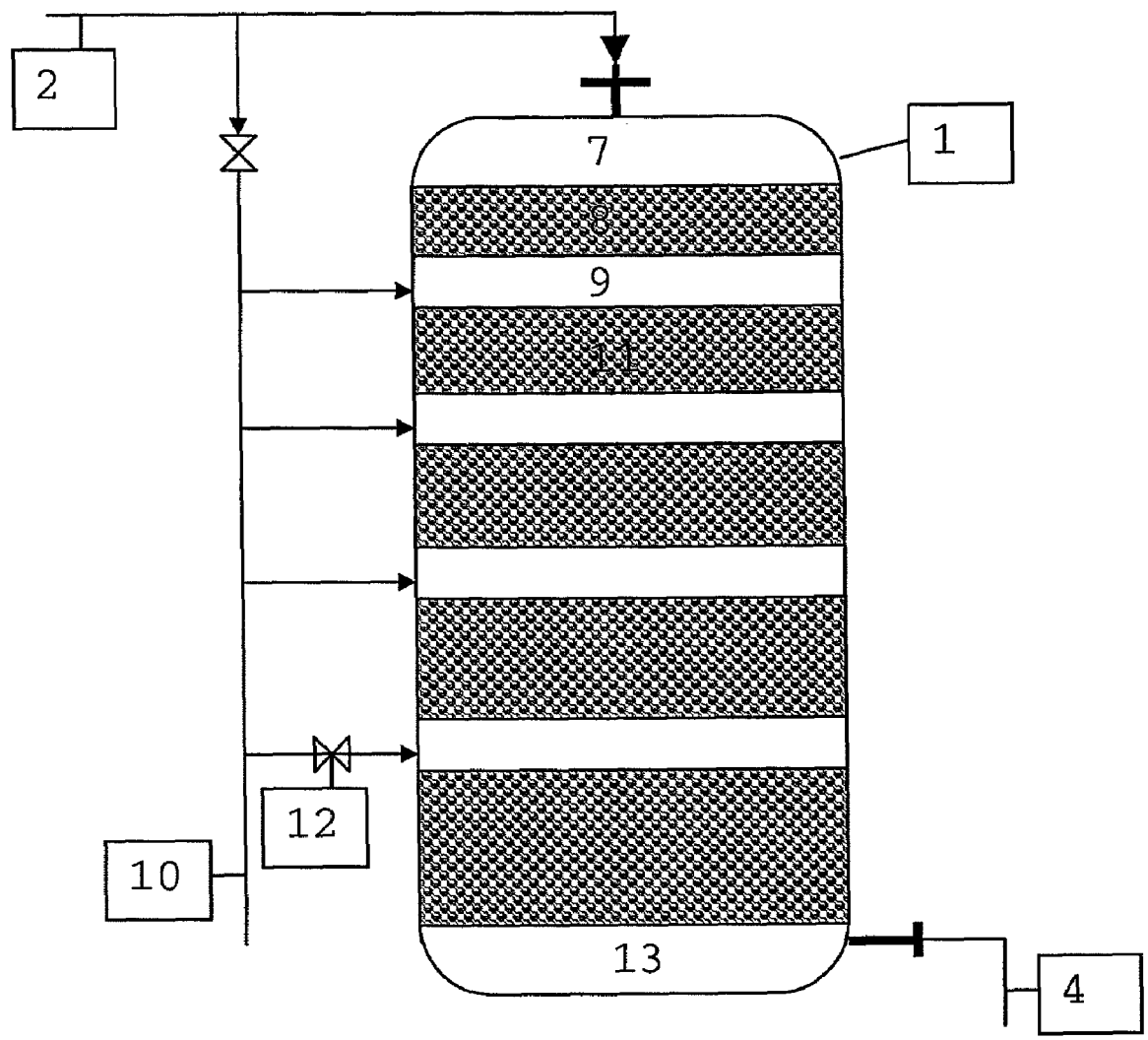

FIG. 2 shows the preferred embodiment of the reactor, according to claim 1. In the reactor 1, n(n=2-25) catalyst beds are accommodated. Preferably, 3-10 catalyst beds (grids) are used. The starting gas mixture 2 enters through the distributor space 7 into the first catalyst bed 8. This first catalyst bed is optionally first covered with a packing of inert materials in the flow direction of the starting gas. For example, alumina spheres or ceramic Raschig rings are used as inert materials. Subsequent to the inert layer is situated the catalyst packing. As a result of the strongly exothermic formation of methyl-mercaptan, in the course of this the temperature in the adiabatic grid increases greatly. After leaving the first grid, the gas mixture is enriched in the distributor space 9 with liquid methanol 10, hydrogen sulphide 10 or optionally the starting gas mixture 2. As a result of the heat of reaction of the first grid, the liquid methanol evaporates without further supply of heat. By this means, the temperature of the gas mixture drops. The gas mixture subsequently flows from the distributor space 9 into the second catalyst bed 11, devices in the distributor space 9 providing for a turbulent flow and a complete mixing of the reactants, which is distributed uniformly to the entire surface of the second catalyst bed. The supply of liquid methanol or optionally hydrogen sulphide or starting gas mixture takes place analogously at n-1, preferably n-2, injection sites between the following catalyst beds of the grid reactor. Optionally, a supply of liquid methanol, hydrogen sulphide or starting gas mixture before the last catalyst bed at the injection site 12 can be dispensed with in order to obtain a complete conversion of methanol in the reaction.

After leaving the grid reactor, the reacted gas mixture is fed to further processing via the collecting space 13 as a product gas stream 4.

Thus, the temperature of a strongly exothermic reaction can be excellently controlled in only one reaction apparatus including an integrated direct heat exchange without additional heat carrier media such as salt melts or steam.

The process scheme shown in FIG. 1 contains the necessary components for carrying out the process according to the invention.

Further modifications and variations will be apparent to those skilled in the art from the foregoing and are intended to be encompassed by the claims appended hereto.

German priority application 10 2005 016 369.6, filed Apr. 5, 2005, is relied on and incorporated herein by reference.

We claim:
1. Process for the continuous catalyzed production of methylmercaptan comprising reacting methanol and hydrogen sulphide in the presence of a catalyst therefor in a gas phase at a temperature of 200 to 600° C. and a pressure of 1.5 to 40 bar, in a plurality of zones
   a) distributing the total amount of the catalyst to at least two zones which are separate from one another, in such a way that the amount of catalyst increases in the flow direction,
   b) supplying a first of said zones with a gaseous mixture comprising methanol and hydrogen sulphide,
   c) feeding methanol and hydrogen sulphide between the first, the second and optionally the further zones in a liquid and/or gaseous form, and
   d) separating off methylmercaptan formed thereby,
   e) the total molar ratio of the amounts of hydrogen sulphide and methanol employed amounting to 1.1:1 to 10:1.

2. The process according to claim 1, wherein said molar ratio is 1.1:1 to 5:1.

3. The process according to claim 1, wherein said reacting is in a grid reactor having 2 to 25 catalyst beds.

4. The process according to claim 3, wherein the reactor has 3 to 10 catalyst beds.

5. The process according to claim 1, wherein catalyst packings in the zones are covered with a layer of packings of inert materials.

6. The process according to claim 5, wherein the first catalyst zone in the flow direction and optionally the last zone are completely or partly coated with an inert material.

7. The process according to claim 1, wherein at least two different catalysts are employed in the zones.

8. The process according to claim 1, wherein the amount of catalyst between the zones varies.

9. The process according to claim 1, wherein the total amount of hydrogen sulphide employed is employed as a gaseous mixture of methanol and hydrogen sulphide.

10. The process according to claim 1, wherein hydrogen sulphide or starting gas is fed into the intermediate space between one or more of the first and second or further zones.

11. The process according to claim 1, wherein the molar ratio of hydrogen sulphide to methanol in the starting gas is 1.1:1 to 20:1.

12. The process according to claim 1, wherein the molar ratio of hydrogen sulphide to methanol in the starting gas is 1.1:1 to 10:1.

13. The process according to claim 1, wherein the molar ratio of hydrogen sulphide to methanol in the starting gas is 3:1 to 10:1.

14. Process according to claim 1, further comprising feeding the methanol into intermediate spaces between the zones in equal amounts.

15. The process according to claim 1, further comprising feeding the methanol into intermediate spaces between the zones in unequal amounts.

16. The process according to claim 1, wherein the last catalyst-containing zone is not supplied with methanol.

17. The process according to claim 2, further comprising flowing methanol and hydrogen sulphide through the catalyst beds in variable directions.

18. The process according to claim 1, further comprising using as catalyst alkali metal tungstates or halide-containing alkali metal tungstates.

19. The process according to claim 18, wherein the catalyst is a halide-free or halide-containing caesium tungstate.

20. The process according to claim 1, further comprising providing a turbulent flow and a uniform distribution and mixing of reactants by means of inert packing materials and/or devices to thereby completely mix the methanol and hydrogen sulphide between the zones.

21. The process according to claim 1, wherein catalyst grids are designed as catalyst beds having radial, square or polygonal geometry and the grids can be individually filled with catalyst or emptied, their design optionally being such that they can be removed from the reactor in modular form.

22. The process according to claim 1, wherein at least one detachable or undetachable connection or opening in the reactor wall is utilized for the simple exchange of the catalyst in the individual grids.

* * * * *